(12) United States Patent
Alizadeh-Khiavi et al.

(10) Patent No.: US 9,050,553 B2
(45) Date of Patent: Jun. 9, 2015

(54) LOW ENERGY, HIGH RECOVERY, RAPID CYCLE KINETIC PSA FOR BIOGAS

(71) Applicant: Air Products and Chemicals, Inc., Allentown, PA (US)

(72) Inventors: Soheil Alizadeh-Khiavi, Burnaby (CA); Jeffrey Alvaji, West Vancouver (CA); Christopher R. McLean, Vancouver (CA)

(73) Assignee: Air Products and Chemicals, Inc., Allentown, PA (US)

( * ) Notice: Subject to any disclaimer, the term of this patent is extended or adjusted under 35 U.S.C. 154(b) by 138 days.

(21) Appl. No.: 13/862,757

(22) Filed: Apr. 15, 2013

(65) Prior Publication Data
US 2013/0247762 A1 Sep. 26, 2013

Related U.S. Application Data

(62) Division of application No. 13/118,186, filed on May 27, 2011, now Pat. No. 8,470,395.

(60) Provisional application No. 61/350,355, filed on Jun. 1, 2010.

(51) Int. Cl.
- *B01D 53/06* (2006.01)
- *B01D 53/047* (2006.01)
- *C12M 1/00* (2006.01)

(52) U.S. Cl.
CPC .......... *B01D 53/0473* (2013.01); *B01D 53/06* (2013.01); *B01D 2253/108* (2013.01); *B01D 2253/308* (2013.01); *B01D 2253/31* (2013.01); *B01D 2253/311* (2013.01); *B01D 2256/245* (2013.01); *B01D 2257/504* (2013.01); *B01D 2258/05* (2013.01); *B01D 2259/4068* (2013.01); *Y02C 10/08* (2013.01); *C12M 47/18* (2013.01)

(58) Field of Classification Search
CPC ............... B01D 53/0473; B01D 53/06; B01D 2253/108; B01D 2253/308; B01D 2253/31; B01D 2253/311; B01D 2256/245; B01D 2257/504; B01D 2258/05; B01D 2259/4068; Y02C 10/08
USPC .............. 96/108, 125, 154; 95/113, 139, 902, 95/903; 423/230, DIG. 30; 502/407; 585/820

See application file for complete search history.

(56) References Cited

U.S. PATENT DOCUMENTS

| | | | | |
|---|---|---|---|---|
| 4,440,871 | A * | 4/1984 | Lok et al. | 502/214 |
| 4,935,580 | A * | 6/1990 | Chao et al. | 95/139 |
| 5,260,243 | A | 11/1993 | Dunne et al. | |
| 6,068,682 | A * | 5/2000 | Kuznicki et al. | 95/130 |
| 7,645,324 | B2 * | 1/2010 | Rode et al. | 95/96 |
| 7,828,875 | B2 * | 11/2010 | Li et al. | 95/51 |
| 8,118,914 | B2 | 2/2012 | Liu et al. | |
| 2003/0121415 | A1 * | 7/2003 | Olson | 95/144 |
| 2005/0022671 | A1 | 2/2005 | Yamazaki et al. | |
| 2005/0054526 | A1 | 3/2005 | Steinke et al. | |
| 2008/0282886 | A1 * | 11/2008 | Reyes et al. | 95/98 |
| 2008/0282892 | A1 * | 11/2008 | Deckman et al. | 96/140 |

* cited by examiner

*Primary Examiner* — Frank Lawrence
(74) *Attorney, Agent, or Firm* — Eric J. Schaal

(57) ABSTRACT

Disclosed herein are embodiments of a rotary gas separation device, such as a rotary pressure swing adsorption device. The rotary pressure swing device can include, for example, a rotor with a plurality of adsorber elements, a stator with a plurality of conduits, and a rotary valve comprising a seal assembly positioned between the rotor and the stator.

11 Claims, 16 Drawing Sheets

FIG. 15

| Cycle speed - CPM | | 30 | | Ph. Angle ° | | Pressure (psia) | |
|---|---|---|---|---|---|---|---|
| Step | Description | # of Beds | Time - sec | Ph. Angle ° | start | end | start | end |
| | | | | | | | | |

| Step | Description | # of Beds | Time - sec | Ph. Angle ° | Ph. Angle ° start | Ph. Angle ° end | Pressure start | Pressure end |
|---|---|---|---|---|---|---|---|---|
| 1 | Production | 2 | 0.1429 | 25.71 | 0 | 25.71 | 105 | 105 |
| 2 | Supply Equalization 1 | 0.5 | 0.0357 | 6.43 | 25.71 | 32.14 | 105 | 80 |
| 3 | Supply Equalization 2 | 0.5 | 0.0357 | 6.43 | 32.14 | 38.57 | 80 | 65 |
| 4 | Supply Equalization 3 | 0.5 | 0.0357 | 6.43 | 38.57 | 45.00 | 65 | 51 |
| 5 | Supply Equalization 4 | 0.5 | 0.0357 | 6.43 | 45.00 | 51.43 | 51 | 36 |
| 6 | Supply Equalization 5 | 0.5 | 0.0357 | 6.43 | 51.43 | 57.86 | 36 | 25 |
| 7 | Reflux 1 | 3 | 0.2143 | 38.57 | 57.86 | 96.43 | 25 | 16 |
| 8 | Reflux 2/Heavy Rinse | 4 | 0.2857 | 51.43 | 96.43 | 147.86 | 16 | 10 |
| 9 | Evacuation | 13 | 0.9286 | 167.14 | 147.86 | 315.00 | 10 | 7.3 |
| 10 | Product Purge | 0.5 | 0.0357 | 6.43 | 315.00 | 321.43 | 7.3 | 7.3 |
| 11 | Equalization 5 | 0.5 | 0.0357 | 6.43 | 321.43 | 327.86 | 7.3 | 25 |
| 12 | Equalization 4 | 0.5 | 0.0357 | 6.43 | 327.86 | 334.29 | 25 | 38 |
| 13 | Equalization 3 | 0.5 | 0.0357 | 6.43 | 334.29 | 340.71 | 38 | 51 |
| 14 | Equalization 2 | 0.5 | 0.0357 | 6.43 | 340.71 | 347.14 | 51 | 65 |
| 15 | Equalization 1 | 0.5 | 0.0357 | 6.43 | 347.14 | 353.57 | 65 | 80 |
| 16 | Backfill/AF | 0.5 | 0.0357 | 6.43 | 353.57 | 360.00 | 80 | 105 |
| | Total | 28 | 2 | 360 | | | | |

LOW ENERGY, HIGH RECOVERY, RAPID CYCLE KINETIC PSA FOR BIOGAS

CROSS-REFERENCE TO RELATED APPLICATIONS

The present application is a divisional application of U.S. Application No. 13/118,186, filed May 27, 2011, and now issued as U.S Pat. No. 8,470,395, which claims the benefit of priority of U.S. Provisional Application No. 61/350,355, filed Jun. 1, 2010, which all are incorporated herein by reference.

FIELD

This disclosure concerns gas separation devices, such as rotary pressure swing adsorption devices that can be used to separate methane from a feed gas, such as biogas.

SUMMARY

Certain disclosed embodiments of the present invention concern a gas separation method for separating carbon dioxide from a gas mixture comprising methane and carbon dioxide using a gas separation device. One exemplary disclosed device comprises a rapid cycle kinetic pressure swing adsorption apparatus utilizing an adsorbent structure having a kinetic adsorbent comprising a molecular sieve with an average pore size of less than about 3.9 Angstroms, and in certain embodiments an average pore size greater than about 3.7 Angstroms. Exemplary molecular sieves include silica alumina phosphate, such as SAPO 34. The crystal size distribution of the SAPO 34 typically is between 10 and 80 microns, and may have an average crystal size of about 40 microns. In certain embodiments, the adsorbent structure is characterized by a macroporosity between about 4% and about 18%, and a macropore size between about 0.001 and about 2 microns. The adsorbent structure may be a parallel passage structured adsorbent comprising a laminated adsorbent sheet. The gas separation device may be a rotary rapid cycle kinetic pressure swing adsorption apparatus.

Embodiments of a pressure swing process cycle for separating carbon dioxide from a gas mixture comprising methane and carbon dioxide also are described. For example, an exemplary process may comprise providing a gas separation device having an adsorbent structure, introducing the gas mixture at an elevated pressure to the adsorbent structure whereby carbon dioxide is preferentially kinetically adsorbed by the adsorbent to produce a methane-rich product gas, delivering the methane-rich product gas from the apparatus, reducing the pressure in the apparatus whereby adsorbed carbon dioxide is desorbed from the adsorbent to produce a carbon-dioxide-rich exhaust gas, and delivering the carbon-dioxide-rich exhaust gas from the apparatus. The process steps may be repeated in a rapid cycle, such as a rapid cycle with cycle speeds of from about 2 cycles per minute (CPM) to at least about 30 CPM, with certain embodiments using a speed of 13 CPM. For certain embodiments, the product producing step time is determined to be longer than 50% of the time required for $CO_2$ to reach total equilibrium on adsorption sites. For certain embodiments, the product producing step time is determined to be shorter than 10% of the time required for $CH_4$ to reach total equilibrium on adsorption sites. The evacuation step time may be determined to be longer than 90% of the time required for $CO_2$ to reach total equilibrium on adsorption sites. And, the ratio of the time spent in the production step to that spent in the evacuation step may be less than 0.15. For certain embodiments, the ratio of the time spent in a single equalization step to that spent in the production step is less than 0.25. The co-current depressurization steps may be applied to generate Reflux 1 recycle streams. Co-current depressurization steps may be vacuum assisted to generate Reflux 2 recycle streams. And, a portion of exhaust gas may be used as a co-current purge stream to recover remaining methane into reflux or recycle streams.

Embodiments of a method for making an adsorbent structure, such as a laminated sheet, for a pressure swing adsorption apparatus also are disclosed. The adsorbent structure may comprise an adsorbent sensitive to sudden increases or decreases in water content. An exemplary embodiment of the method comprises preparing an aqueous slurry, comprising up to 50% water, and a sensitive adsorbent. A substrate, such as a sheet, is coated with the aqueous slurry. The coated substrate is dried to produce the adsorbent structure.

Drying may comprise plural drying steps, such as first, second, and third drying stages in sequence. For these embodiments, the rate of drying in the second drying stage typically is slower than that in the first drying stage and the rate of drying in the first drying stage typically is slower than that in the third drying stage. The first drying stage may involve: drying at a drying rate removing less than or equal to 30% weight of water per minute; drying at less than or equal to 40° C. on exit of dryer; and/or may comprise drying such that 25 to 30% of the water in the coated substrate is removed before the drying process is discontinued. For certain embodiments, the second drying stage may comprise: drying at a rate removing less than or equal to 5% weight of water per day; drying at ambient temperature; and/or drying such that 5 to 10% of the water in the coated substrate is removed before drying is discontinued. For certain embodiments, the third drying stage may comprise: drying at a drying rate removing greater than or equal to 10% weight of water per minute; drying at a temperature above about 130° C.; and/or drying such that 5 to 10% of the water in the coated substrate is removed before drying is discontinued. For certain embodiments, up to 10% of the water in the coated substrate remains in the adsorbent in the adsorbent structure after drying.

The method also may include exposing sensitive adsorbent to water vapor, such as ambient humid air, before preparing the slurry. This process slowly adds water to the adsorbent before the slurry is prepared. The exposing step typically occurs over a period of from about 4 to about 7 days. And from about 20% to about 30% by weight water may be adsorbed by the sensitive adsorbent.

BRIEF DESCRIPTION OF THE DRAWINGS

FIG. 15 is a table of the process steps, including relative timing and process pressures.

DETAILED DESCRIPTION

Figure 1:
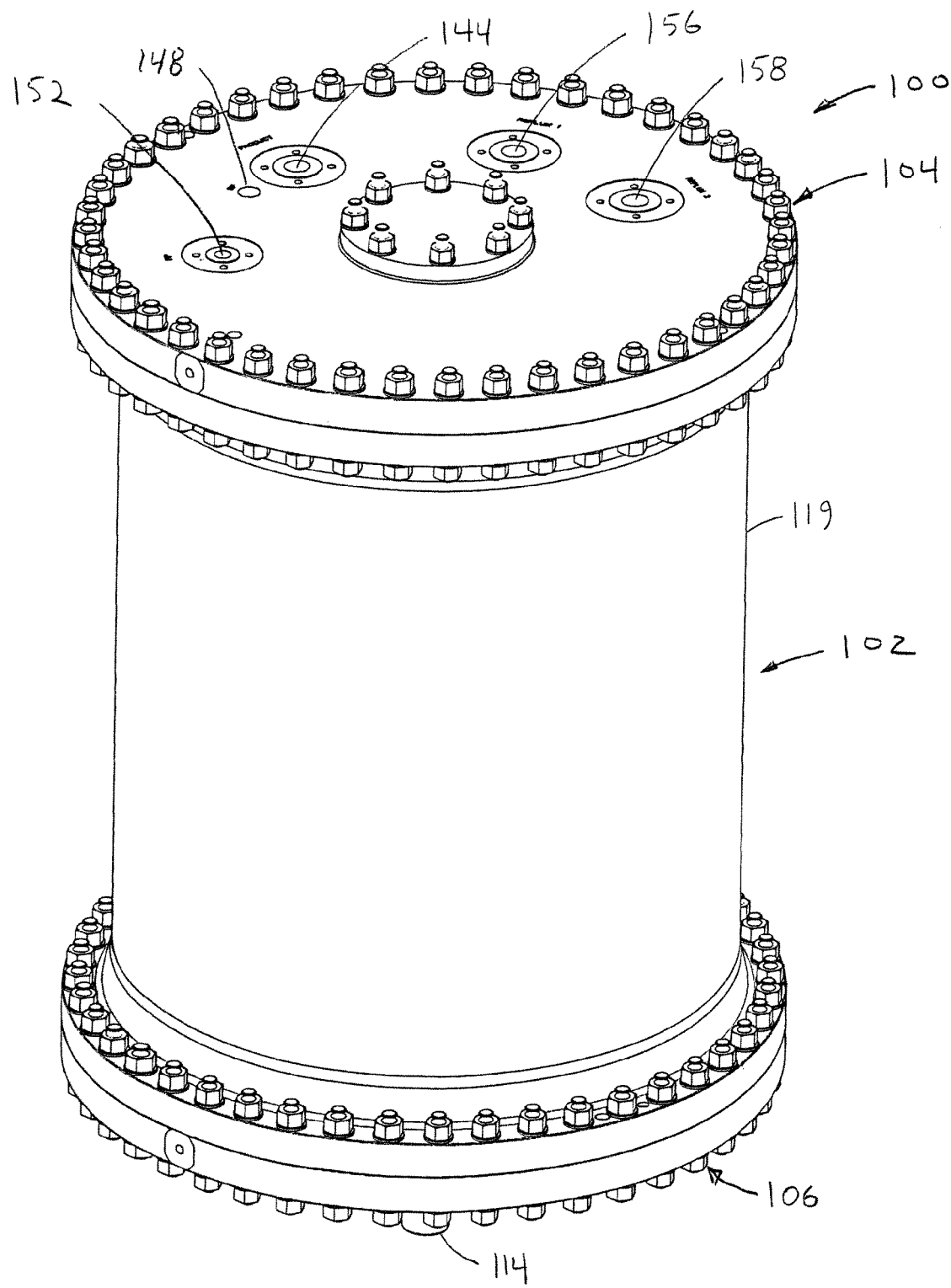
FIG. 1 is a perspective view of one pressure swing embodiment of the disclosed rotary gas separation device.

Unless otherwise explained, all technical and scientific terms used herein have the same meaning as commonly understood by one of ordinary skill in the art to which this disclosure pertains. The singular terms "a," "an," and "the" include plural referents unless the context clearly indicates otherwise. Similarly, the word "or" is intended to include "and" unless the context clearly indicates otherwise. The term "includes" means "comprises." All patents and publications mentioned herein are incorporated by reference in their entirety, unless otherwise indicated. In case of conflict as to the meaning of a term or phrase, the present specification, including explanations of terms, will control. Directional terms, such as "upper," "lower," "top," "bottom," "front," "back," "vertical," and "horizontal," are used herein to express and clarify the relationship between various elements. It should be understood that such terms do not denote absolute orientation (e.g., a "vertical" component can become horizontal by rotating the device). The materials, methods, and examples recited herein are illustrative only and not intended to be limiting.

Exemplary Device Configuration

FIGS. 1-13 show various views of one embodiment of the disclosed rotary pressure swing device. The illustrated rotary pressure swing device 100 includes a rotor assembly 102 positioned between an upper stator assembly 104 and a lower stator assembly 106. As best seen in FIG. 4, a motor (not shown), can be used to rotate an axle 114 connected to a rotor 116 within the rotor assembly 102. Below the rotor 116, a bottom bearing 117 supports the mass of the rotor 116 and permits rotation of the rotor 116. Above the rotor, a top bearing 115 aligns the axis of the rotor 116 with the axis of the rotary pressure swing device 100. The rotor 116 is contained within a rotor housing 119.

The rotor 116 is useful for rotating adsorber elements 122. Rotation of the rotor 116 cycles fluid flow through each adsorber element 122 as an adsorber element is rotated to receive fluid flow through a fluid port. While various processes can be implemented using disclosed embodiments of rotary pressure swing devices, for one exemplary process each complete cycle includes a high-pressure adsorption stage and a lower-pressure exhaust stage. In addition, some embodiments include one or more reflux stages between the high-pressure adsorption stage and the lower-pressure exhaust stage. Embodiments also can include one or more feed pressurization stages prior to the high-pressure adsorption stage and/or one or more product purge stages prior to the low pressure exhaust stage. Additional details regarding the disclosed rotary pressure swing processes are provided later in this disclosure under the subheading "Exemplary Process Specifications." Pressure transducers (not shown) can be included at one or both ends of representative adsorber elements 122 to generate data for monitoring and calibrating the process cycles. Signals from the pressure transducers can be fed to a controller.

The illustrated embodiments of rotary pressure swing device 100 are configured to perform one complete PSA cycle for each rotation of the rotor 116. Other embodiments can be configured to perform a greater number of PSA cycles per rotation, such as two, three or four. Including more than one PSA cycle per rotation can be advantageous for efficient product production and for other process considerations, such as to distribute pressure loads more evenly around the circumference of the device and to reduce the overall rotation speed of the device for a given PSA cycle speed.

Figure 2:
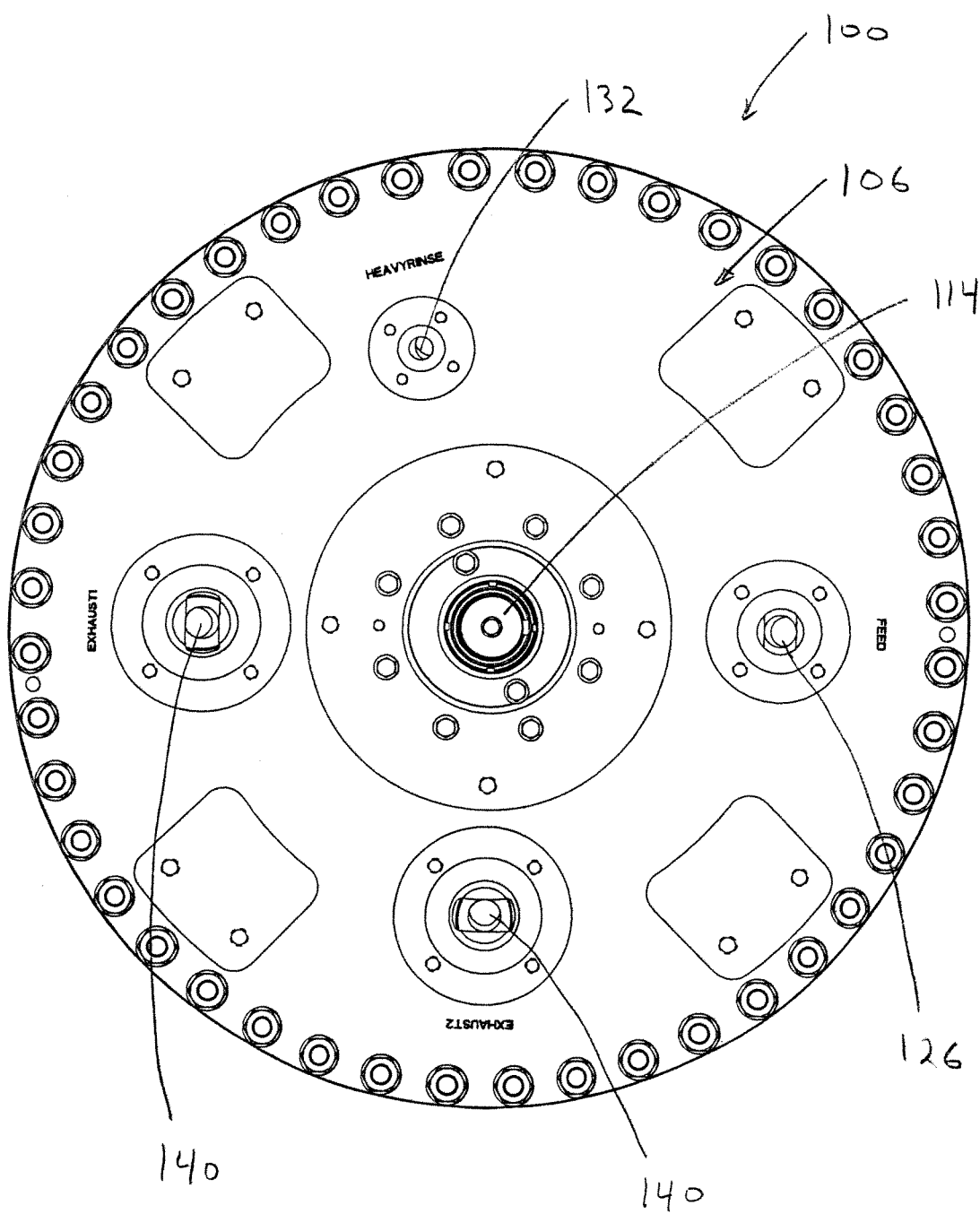
FIG. 2 is a plan view of the bottom of the rotary pressure swing device embodiment shown in FIG. 1.

As best seen in FIG. 2, the feed mixture flows into feed port 126. The lower stator assembly 106 also includes one lower reflux port 132.

The illustrated embodiments of the PSA device 100 also typically include exhaust ports 140. There may be one, two or more exhaust ports. Multiple exhaust ports can be used to reduce the pressure drop through the exhaust ports by dividing the flow and reducing the gas velocity.

Figure 3:
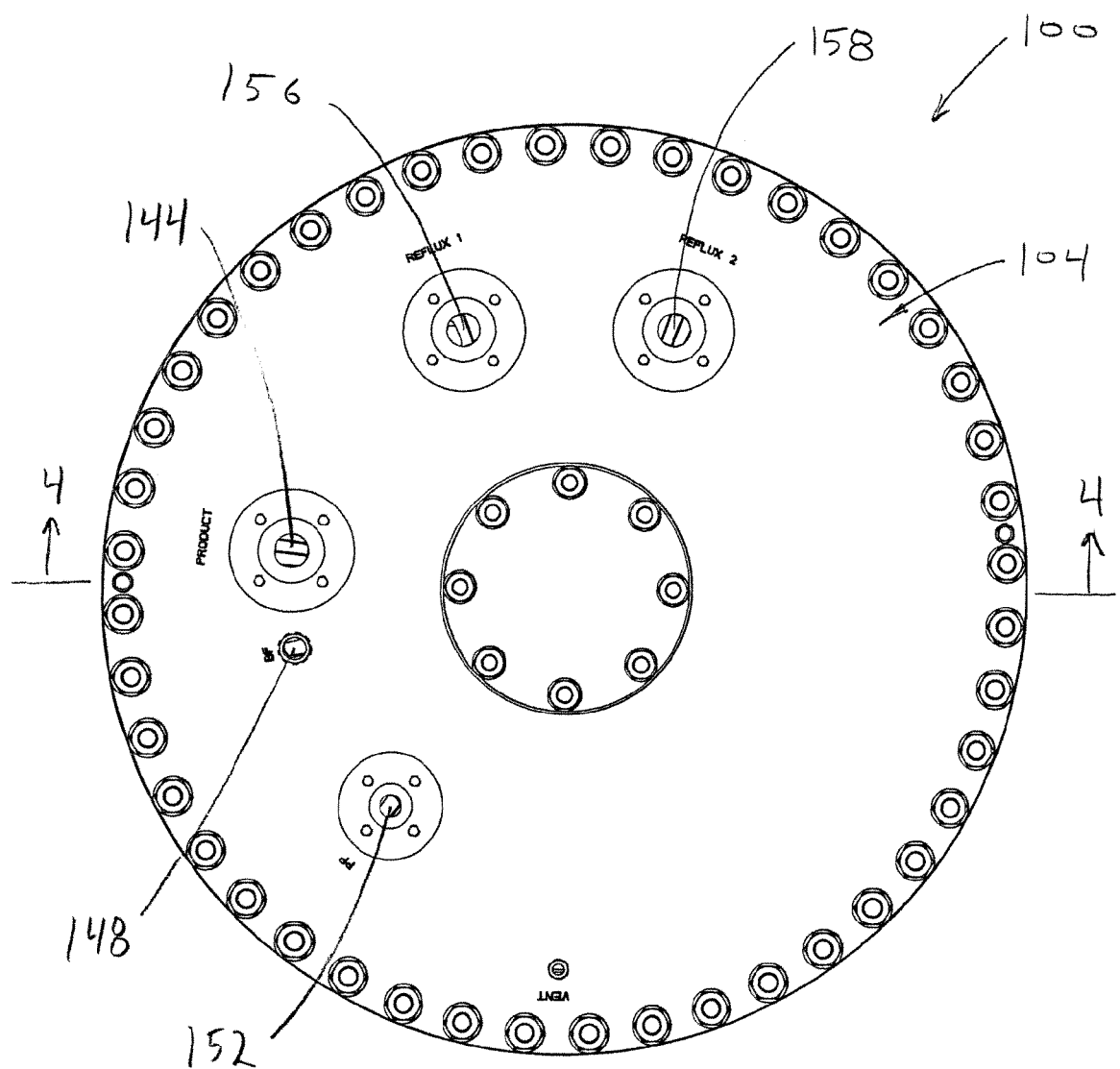
FIG. 3 is a plan view of the top of the rotary pressure swing device embodiment shown in FIG. 1.
Figure 4:
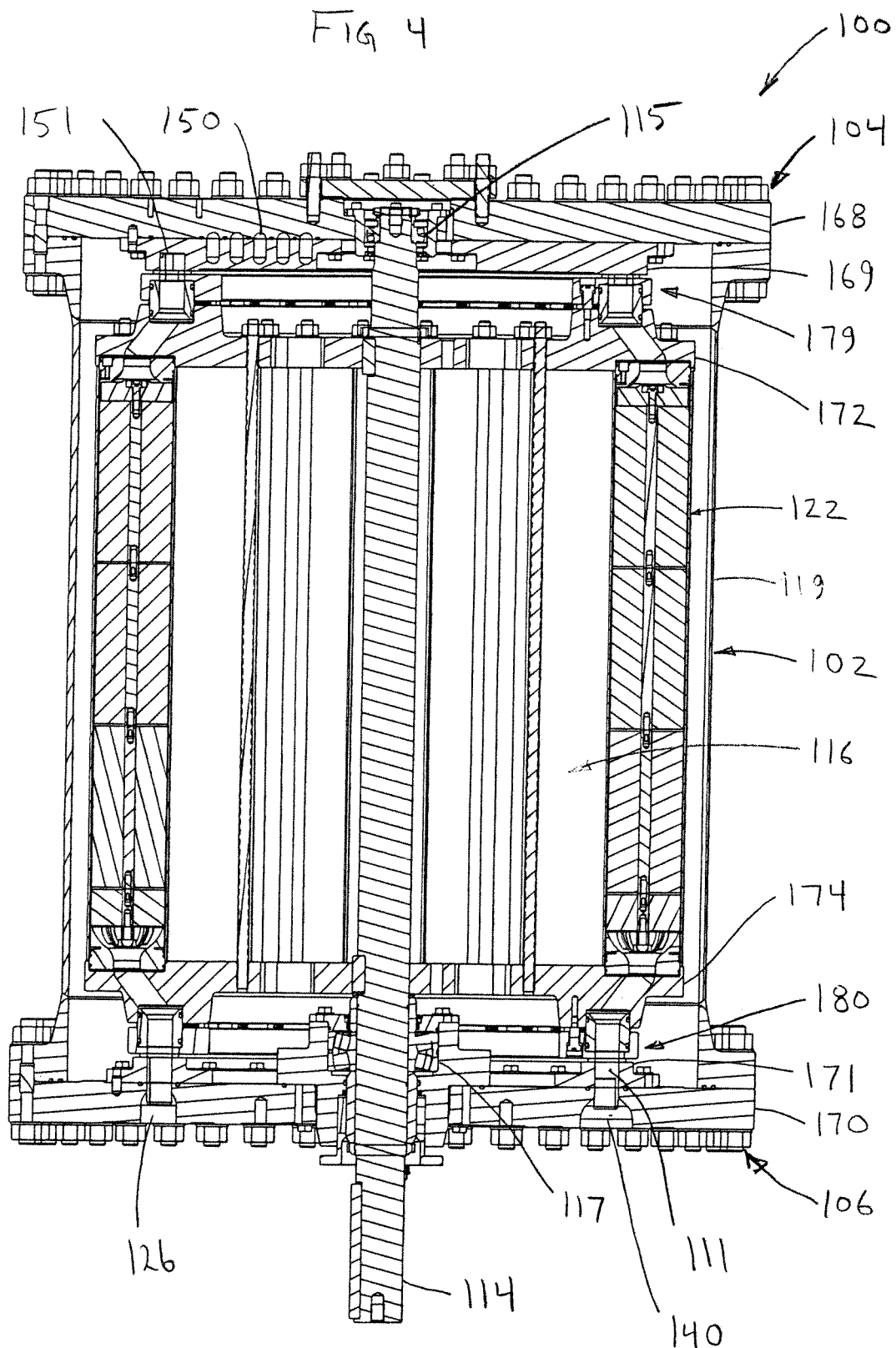
FIG. 4 is a cross-sectional view of the rotary pressure swing device embodiment shown in FIG. 1 taken along the line 4-4 in FIG. 3.

The configuration of the upper stator assembly 104 is best seen in FIG. 3. Product exits the rotary pressure swing device 100 via a product port 144. In operation, a product pressurization conduit (not shown) conveys fluid from the product port 144 to the product pressurization port 148. Flow through the product pressurization conduit (not shown) can be controlled by a product pressurization conduit valve (not shown). In operation, a product purge conduit (not shown) conveys fluid from the product port 144 to the product purge port 152, to deliver purge fluid, which can be product fluid, to the adsorber elements 122. Flow through the product purge conduit (not shown) can be controlled by a product purge conduit valve (not shown). The upper stator assembly 104 also includes upper reflux #1 port 156 and upper reflux #2 port 158.

As best seen in FIG. 4, the upper stator plate 168 and the lower stator plate 170 are effectively coupled to the rotor housing 119. Attached to the upper stator plate 168 is an upper seal counter-face 169, and attached to the lower stator plate 170 is a lower seal counter-face 171. Reflux channels 150 in the upper stator plate 168 and upper seal counter-face 169 can be used to convey reflux flows from one stage in the process to another, according to the required process. Product wear plate channels 151 convey fluid from the rotor 116 to ports 152, 148, 144, 156, and 158 in the product stator assembly 104, according to the required separation process. Feed wear plate channels 111 convey fluid from the rotor 116 to ports 126, 140, and 132 in the feed stator assembly 106, according to the required separation process. Additional details regarding the disclosed rotary pressure swing processes are provided later in this disclosure under the subheading "Exemplary Process Specifications."

The upper seal assembly 179 is positioned between the upper seal counter-face 169 and the upper rotor end plate 172. Similarly, a lower seal assembly 180 is positioned between the lower seal counter-face 171 and the lower rotor end plate 174.

Figure 5:
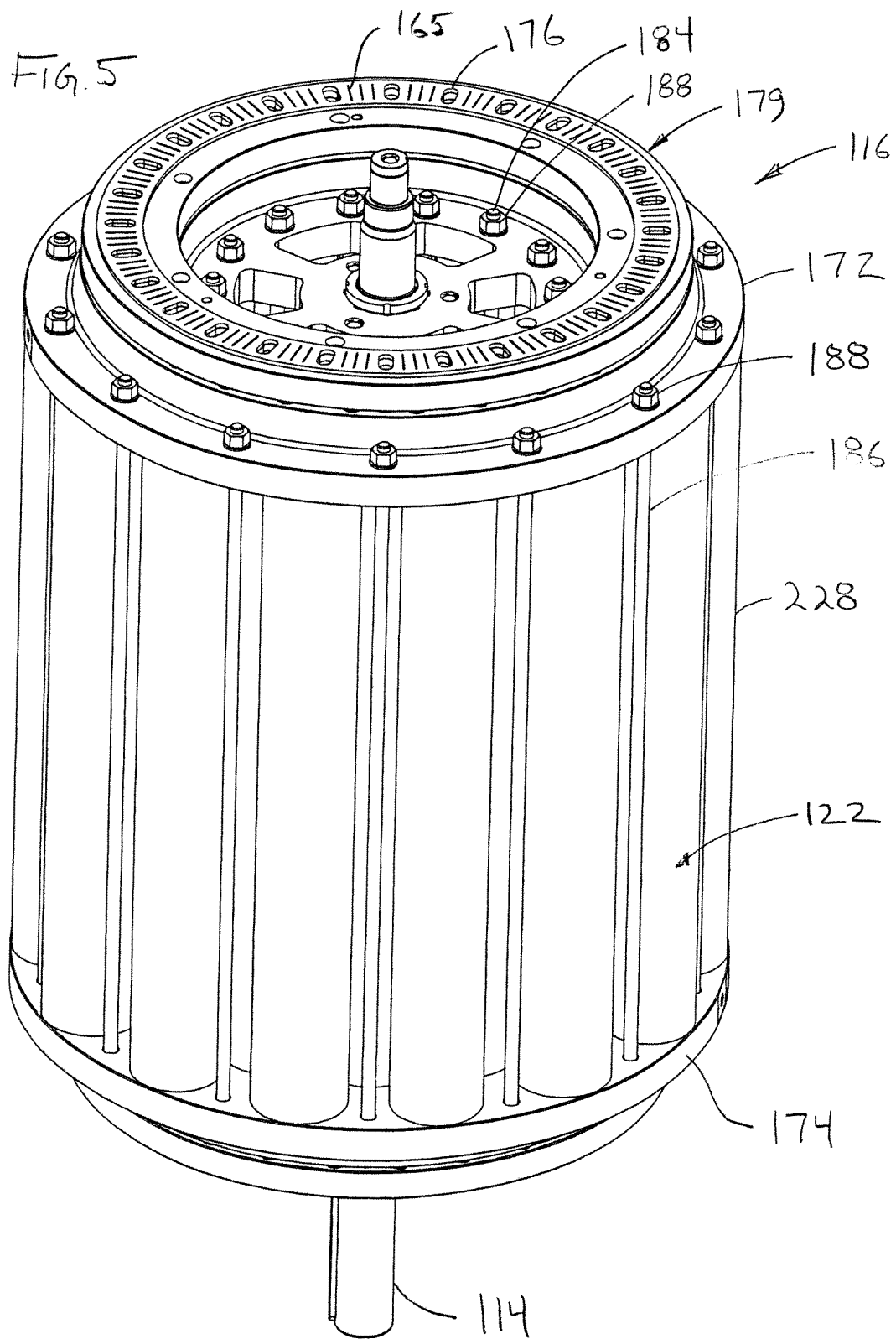
FIG. 5 is a perspective view of the rotor of the rotary pressure swing device embodiment shown in FIG. 1.
Figure 7:
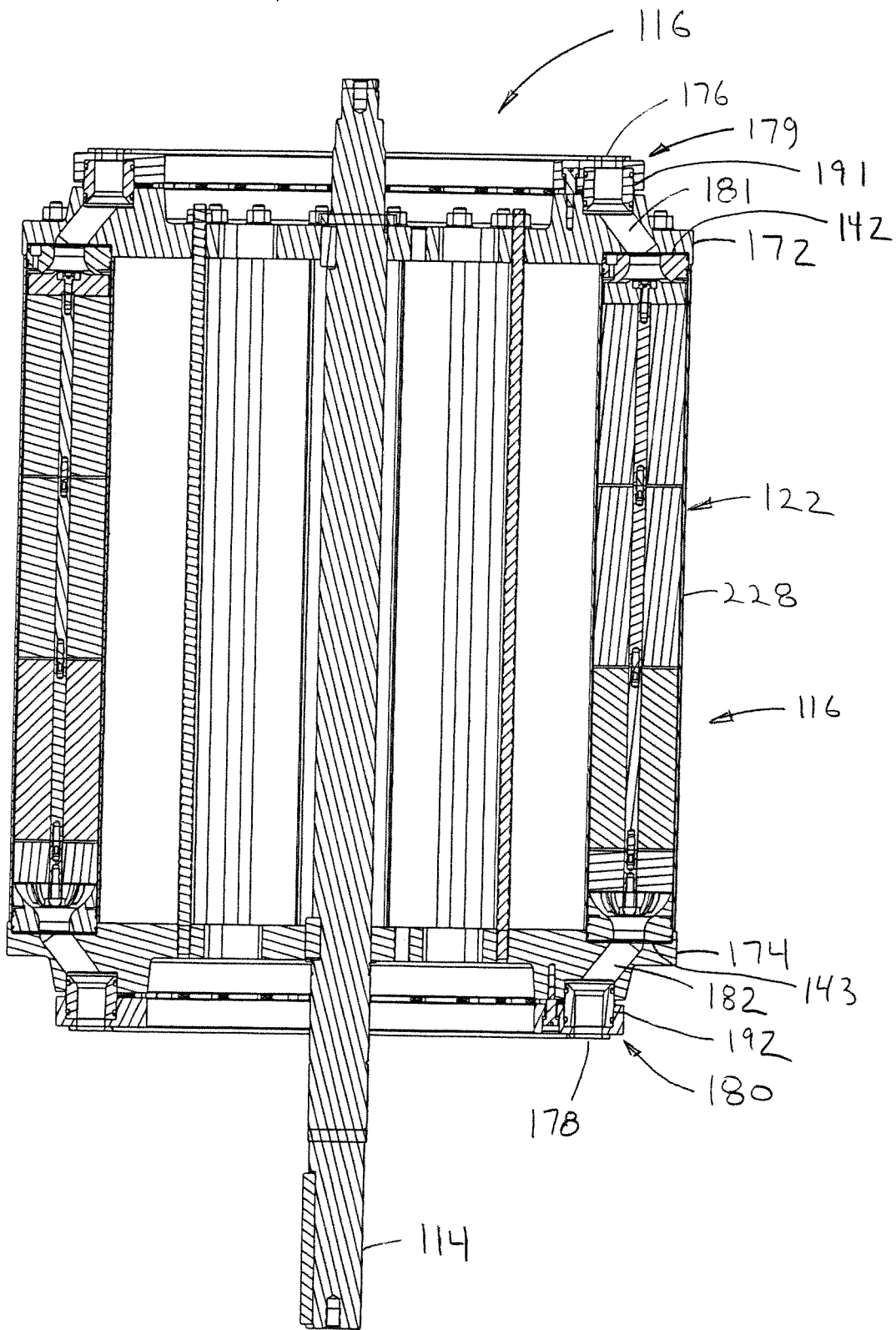
FIG. 7 is a cross-sectional view of the rotor of the rotary pressure swing device embodiment shown in FIG. 1 taken along the line 7-7 in FIG. 6.

FIG. 5 is an isometric view of the rotor 116. The rotor 116 includes an upper rotor end plate 172 and a lower rotor end plate 174, both centered and fixed rotationally to axle 114. A ring of inner tie rods 184 and a ring of outer tie rods 186 secure the upper rotor endplate 172 to the lower rotor endplate 174. The inner and outer tie rods 184, 186 are secured at their bottom end by threading them into a partially threaded hole in the lower rotor endplate 174. The inner and outer tie rods 184, 186 are secured at their top end with nuts 188 pressing against the outer surfaces of the upper rotor end plate 172. As best seen in FIG. 7, once secured, the top and bottom ends of the bed tube 228 press against the inner surfaces of the upper and lower rotor end plates 172, 174, respectively. This secures the adsorber elements 122 in the rotor 116 and prevents them from moving. Also shown in FIG. 5 is the product seal assembly 179. Additional details regarding the disclosed rotary pressure swing seals are provided later in this disclosure under the subheading "Exemplary Seals."

Figure 6:
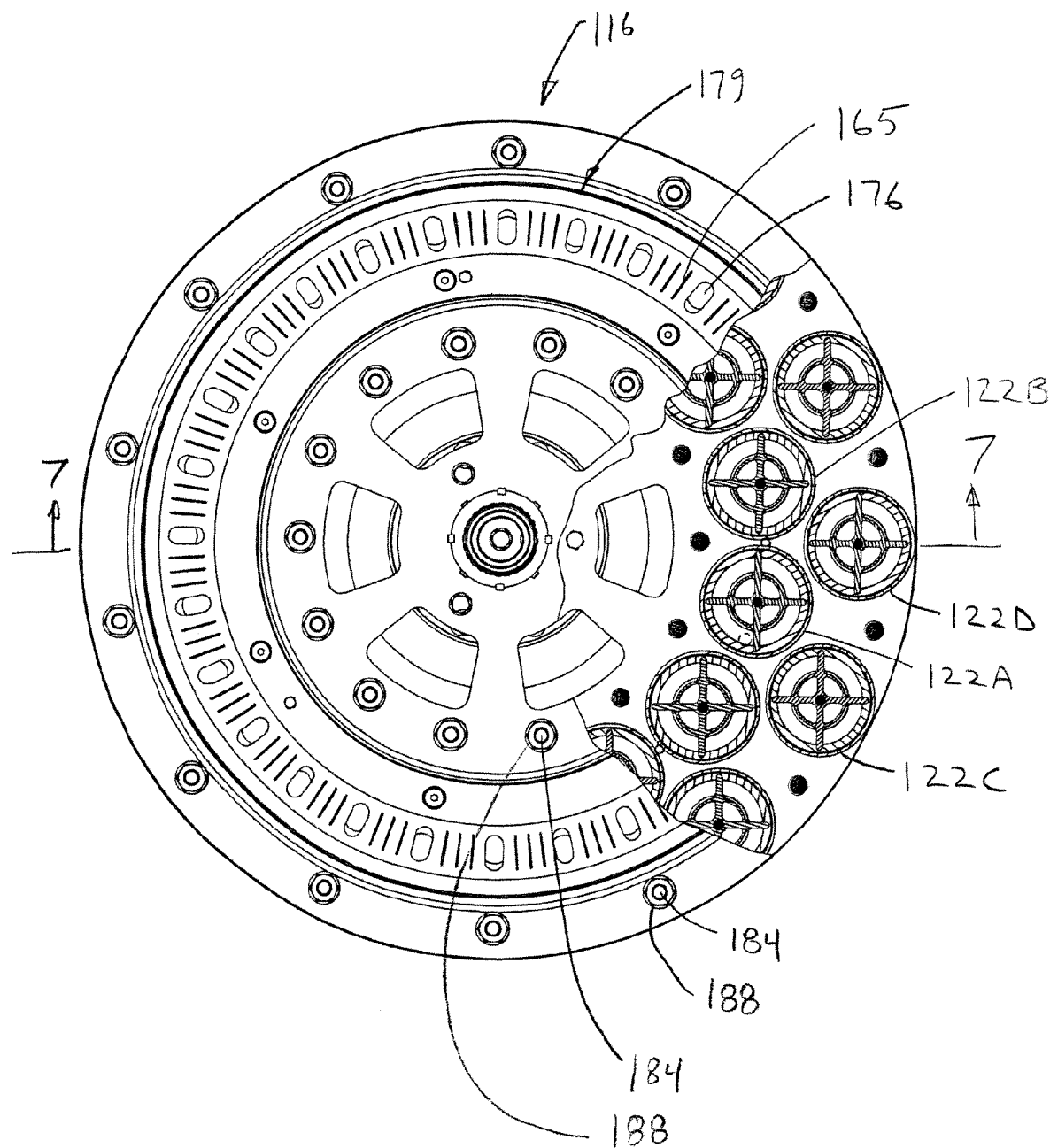
FIG. 6 is a plan view of the top of the rotor of the rotary pressure swing device embodiment shown in FIG. 1 with a portion cut away to show a cross-section taken through the adsorber elements.

FIG. 6 includes a partial cut-away showing the arrangement of the adsorber elements 122 in the rotor 116 for the illustrated embodiment of PSA device 100. Packing efficiency may be improved by using a greater number of relatively small adsorber elements 122 in multiple rows, rather than a smaller number of relatively large adsorber elements arranged in a single row. This positions the adsorber elements 122 in a nested, interlocking, radial pattern. In the illustrated embodiment, the rotary pressure swing device 100 includes 28 adsorber elements 122 in two concentric rows of 14 adsorber elements 122. Of course, different embodiments can have different numbers of adsorber elements in different spatial arrangements. Many design features of the rotary pressure swing device 100 are considered when selecting the arrangement of the adsorbent elements 122. Such features include the overall pitch circle diameter of the upper and lower seal assemblies 179, 180, the rotation speed, the gas flow efficiency, and dead gas volume. For illustration, inner adsorber elements 122A, 122B, and outer adsorber elements 122C, 122D are shown. A portion of adsorber element 122A in the inner pair is positioned between adsorber elements 122C and 122D in the outer pair and a portion of adsorber element 122D in the outer pair is positioned between adsorber elements 122A, 122B in the inner pair. This nested configuration allows for closer packing of adsorber elements 122 than would be possible if the pairs of adsorber elements were arranged in a uniform ring and allows for uniform fluid flow to all of the adsorber elements 122. An even number of adsorber elements 122 facilitates this arrangement.

FIG. 7 shows a cross sectional view of rotor 116. Fluid from the upper ends of adsorber elements 122 is conveyed via angled drillings 181 and seal connectors 191 to the upper rotor apertures 176. These upper rotor apertures 176 communicate with product wear plate channels 151.

Fluid from the lower ends of adsorber elements 122 is conveyed via angled drillings 182 and seal connectors 192 to the lower rotor apertures 178. These lower rotor apertures 178 communicate with feed wear plate channels 111.

Exemplary Seals

Figure 8:
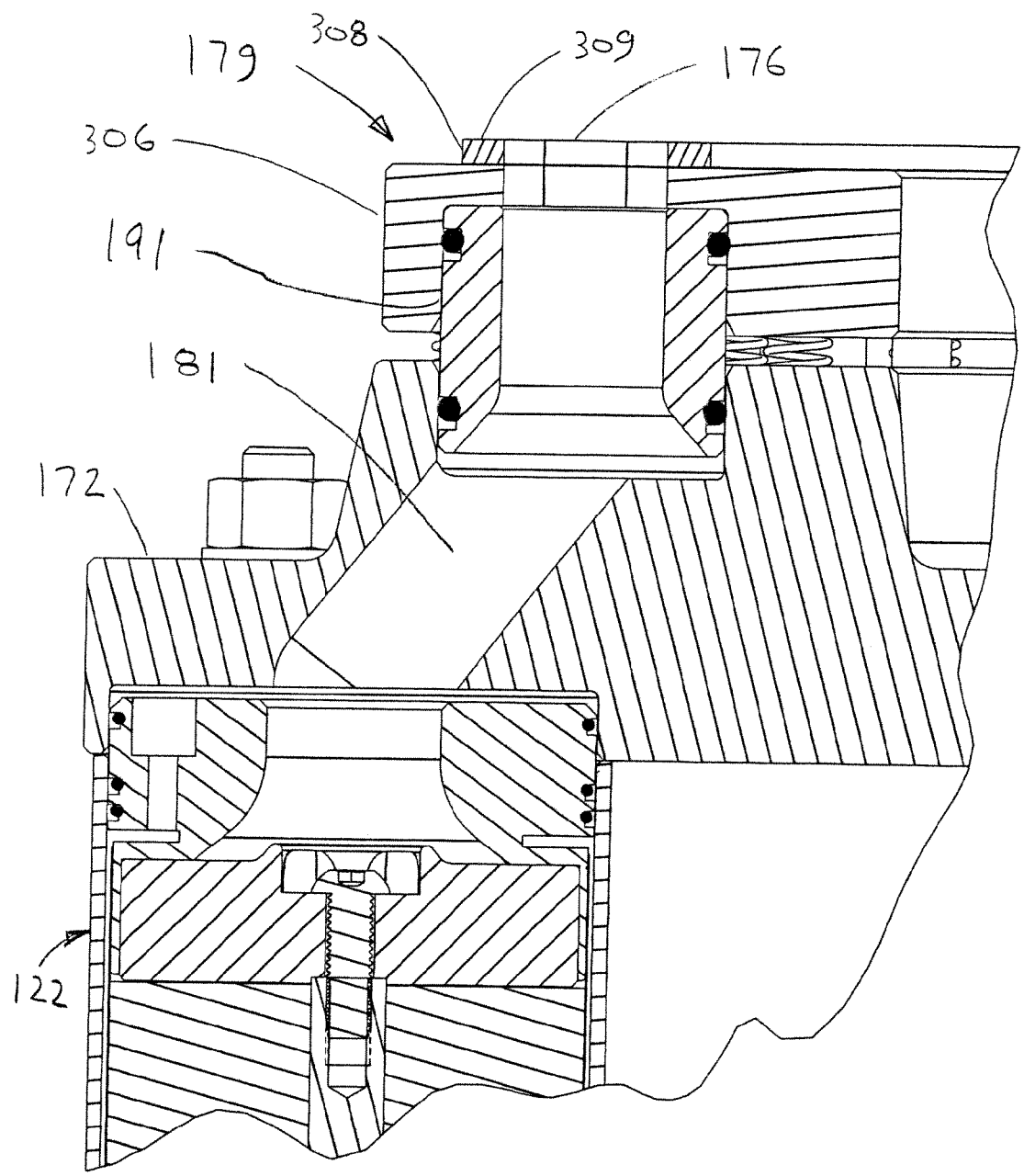
FIG. 8 is a detailed view of the flow passage and seal shown in FIG. 7.
Figure 9:
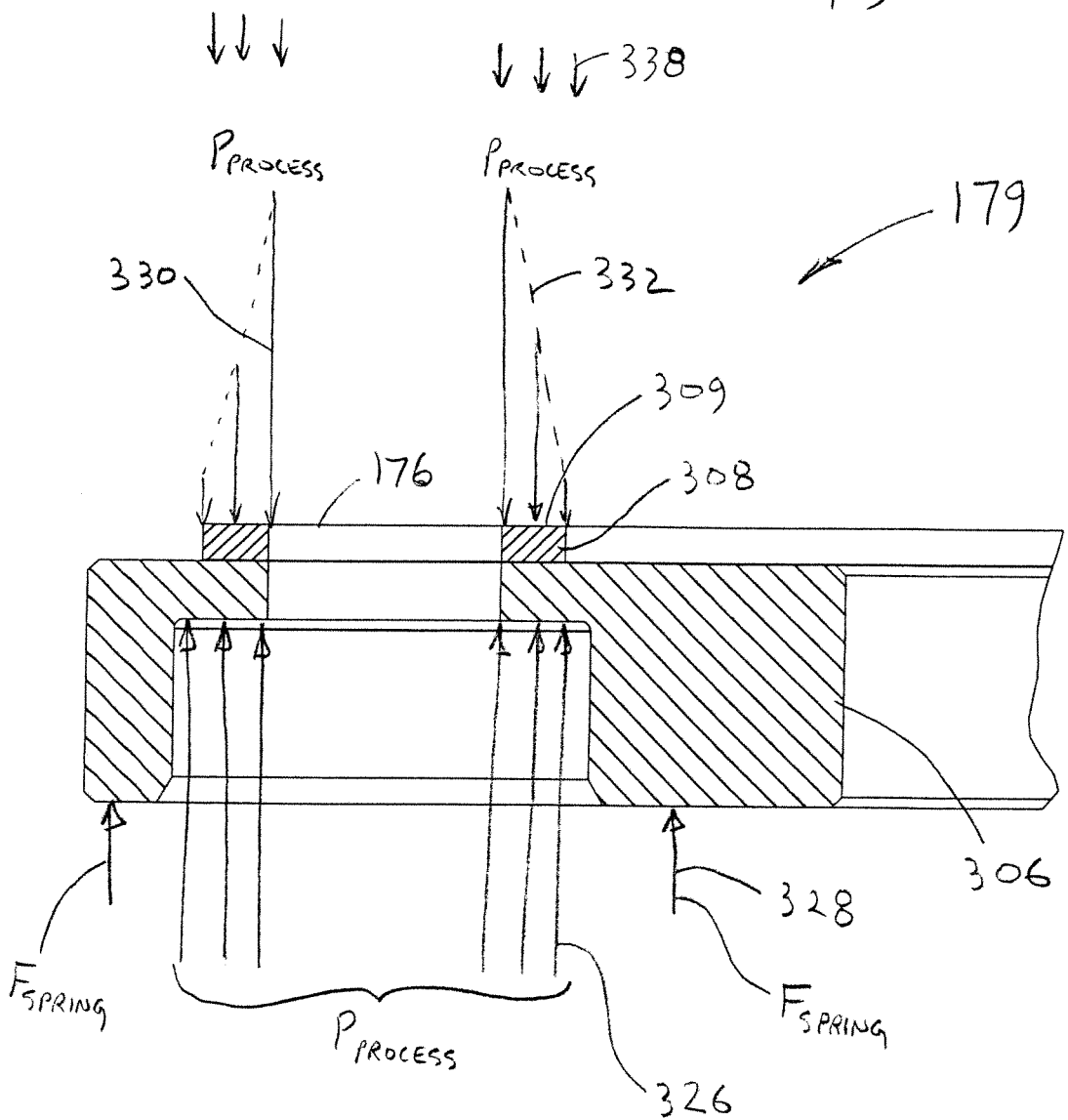
FIG. 9 is a schematic cross sectional view showing the pressures and forces acting on the seal assembly shown in FIG. 8 during operation of the rotary pressure swing device.

FIGS. 8-9 illustrate an embodiment of the upper seal assembly 179 shown in FIG. 7. In the rotary pressure swing device 100, the upper seal assembly 179 is attached to the upper rotor endplate 172, and rotates with the rotor 116 during operation. The lower seal assembly 180 (FIG. 7) is comparable in structure to the upper seal assembly 179, so only the upper seal assembly is illustrated and described in detail. Both assemblies however serve as part of rotary distributor valves to distribute gases to and from the various adsorber elements at appropriate times during the pressure swing cycle, and yet also provide an adequate seal against leakage of these gases. As the rotor rotates between the wear plates (seal counterfaces), valve action is provided as apertures in the wear plates and seal assemblies come into and then out of alignment.

As shown in FIG. 8, the upper seal assembly 179 is a "floating seal," as the upper seal assembly 179 is free to move vertically relative to the rest of the rotor 116. Upper seal assembly 179 is composed of a seal backer 306 and a wear portion 308 with a sealing face 309. Sliding contact with the upper seal counter-face 169 occurs at the sealing face 309.

It is advantageous to provide sufficient closing force at the sealing face 309 to prevent substantial material loss, while still minimizing friction that can increase torque and cause excessive wear on the sliding parts. The illustrated upper seal assembly 179 includes several features that facilitate achieving an appropriate closing force. FIG. 9 is a schematic, cross sectional view showing the pressures and forces acting on different surfaces of the upper seal assembly 179 during operation of the rotary pressure swing device 100. Arrows 326 (one numbered in FIG. 9) indicate the "process pressure," which is the pressure of the process gas in the adsorber elements 122. The pressure of the process gas varies significantly at different stages of the PSA cycle, so the process pressure indicated by arrows 326 also varies. Arrows 328 (one numbered in FIG. 9) indicate the force on the seal backer 306 exerted by an inner row of springs (not shown), and an outer row of springs (not shown), which are placed between the seal backer 306 and product rotor endplate 172. Arrows 330 indicate the "opening pressure," which is the pressure against the sealing face 309 and upper seal counter-face 169 that is exerted by leakage of the process gas. In the illustrated example, the opening pressure diminishes with further distance from the rotor aperture 176, as indicated by the relative lengths of the arrows 330.

Directly adjacent to the rotor aperture 176, the opening pressure is substantially equal to the process pressure. At the far edge of the sealing face 309, the opening pressure is substantially equal to the pressure inside the rotor housing 119. The opening pressure across the sealing face 309 from the rotor aperture 176 to the far edge can decrease according to a variety of profiles. In some implementations, the profile is linear, as shown by line 332 in FIG. 9. The profile also can be convex or concave. The total opening pressure across the sealing face 309 from the rotor aperture 176 to the far edge can be calculated using modeling.

The variables that can be adjusted to achieve the target net closing force include the spring force and the area on the bottom surface of the seal backer 306 that is exposed to the process pressure 326.

A variety of materials can be used in embodiments of the disclosed upper sealing assembly 179. Material properties such as coefficient of thermal expansion, stiffness (modulus and thickness), and thermal conductivity are useful to consider. Overall stiffness of the backer 306 typically promotes stable operation over time. Some compliance, however, is desirable to accommodate imperfections in the flatness of the upper seal counter-face 169.

In some embodiments, the wear portion 308 is made of a polymeric material or materials, such as filled polytetrafluoroethylene, and the remainder of the seal backer 306 is made of a metal, metal alloy, or combinations thereof, such as carbon steel. The wear portion 308 can be coupled to the remainder of the seal backer 306 by any suitable means, such as by using epoxy.

While the PSA device is operating, hot flowing gases and friction heat the various components making up the rotary face seal. Temperature gradients can form and the components will expand and can distort. In particular, if the thermal expansion coefficient of the wear portion 308 is significantly greater than that of seal backer 306, the former wants to expand more than the latter. But, because they are bonded together, the wear portion 308 then can get distorted. Both a coning (developing a convex shape over the diameter of the seal ring) and a crowning (developing a convex shape over the width of the seal face) of the seal assembly 179 and the seal face 309 can occur.

We have discovered that this crowning can be reduced substantially and thus the seal can be stabilized against temperature variations by incorporating certain anti-crowning features into the seal ring. The anti-crowning relief slot feature 165 (seen best in FIGS. 5 and 6) can comprise a blind relief slot in the middle of the seal face such that the slot does not go all the way through the seal face to the backing ring. The seal ring may comprise a plurality of such blind relief slots.

Exemplary Adsorber Elements

Figure 10:
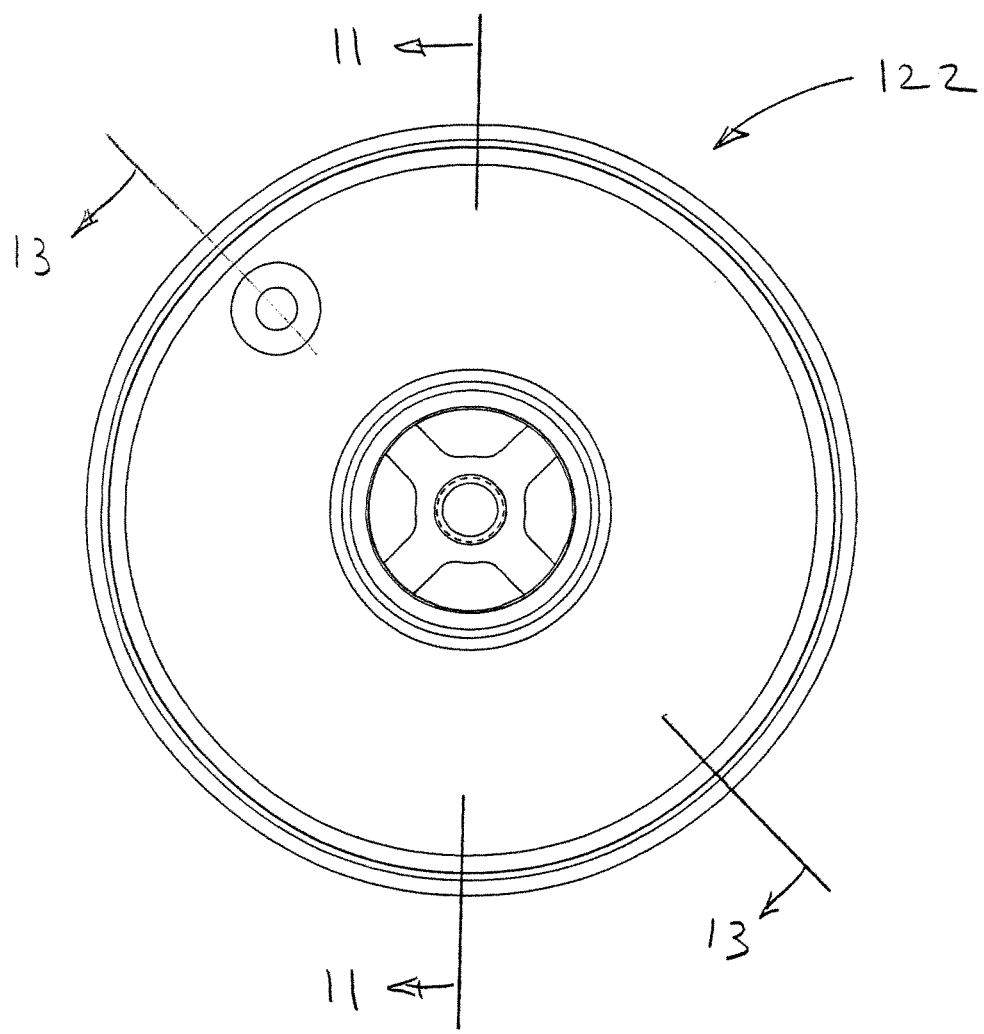
FIG. 10 is a plan view of the top end of one embodiment of an adsorber element suitable for use with embodiments of the disclosed rotary pressure swing device.
Figure 11:
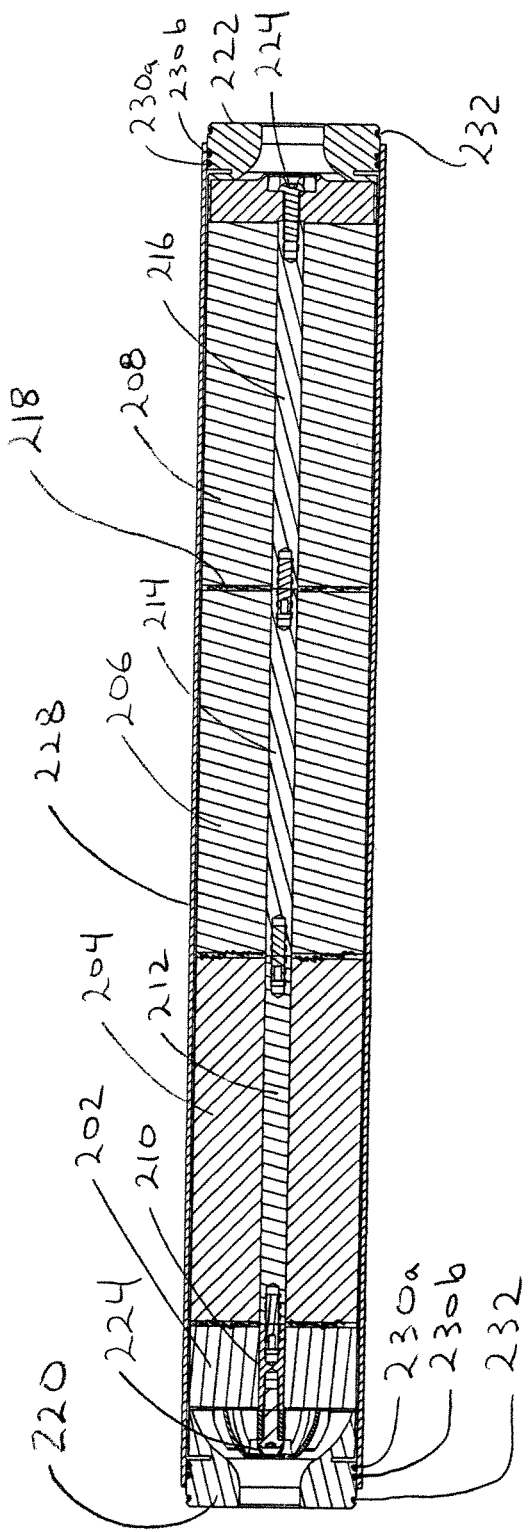
FIG. 11 is a cross sectional view of the adsorber element embodiment shown in FIG. 10 taken along the line 11-11.
Figure 12:
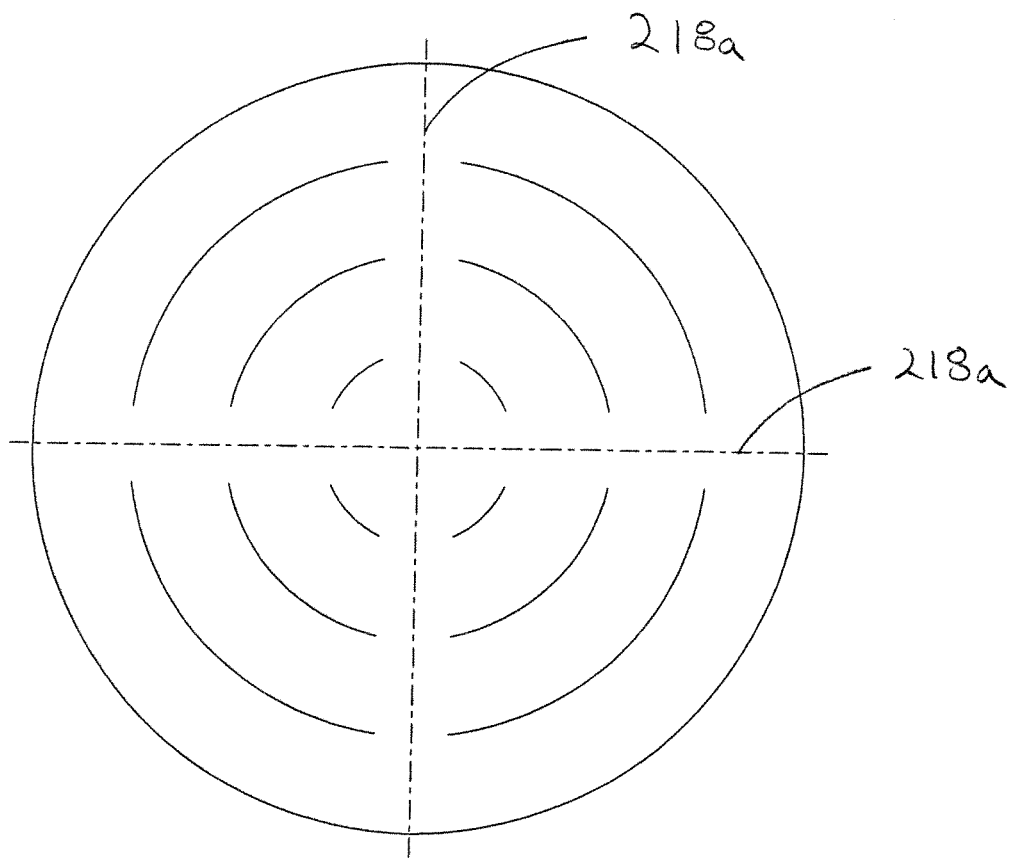
FIG. 12 is a plan view of a spacer cross support structure between laminate structures in the adsorber element embodiment of FIG. 11.
Figure 13:
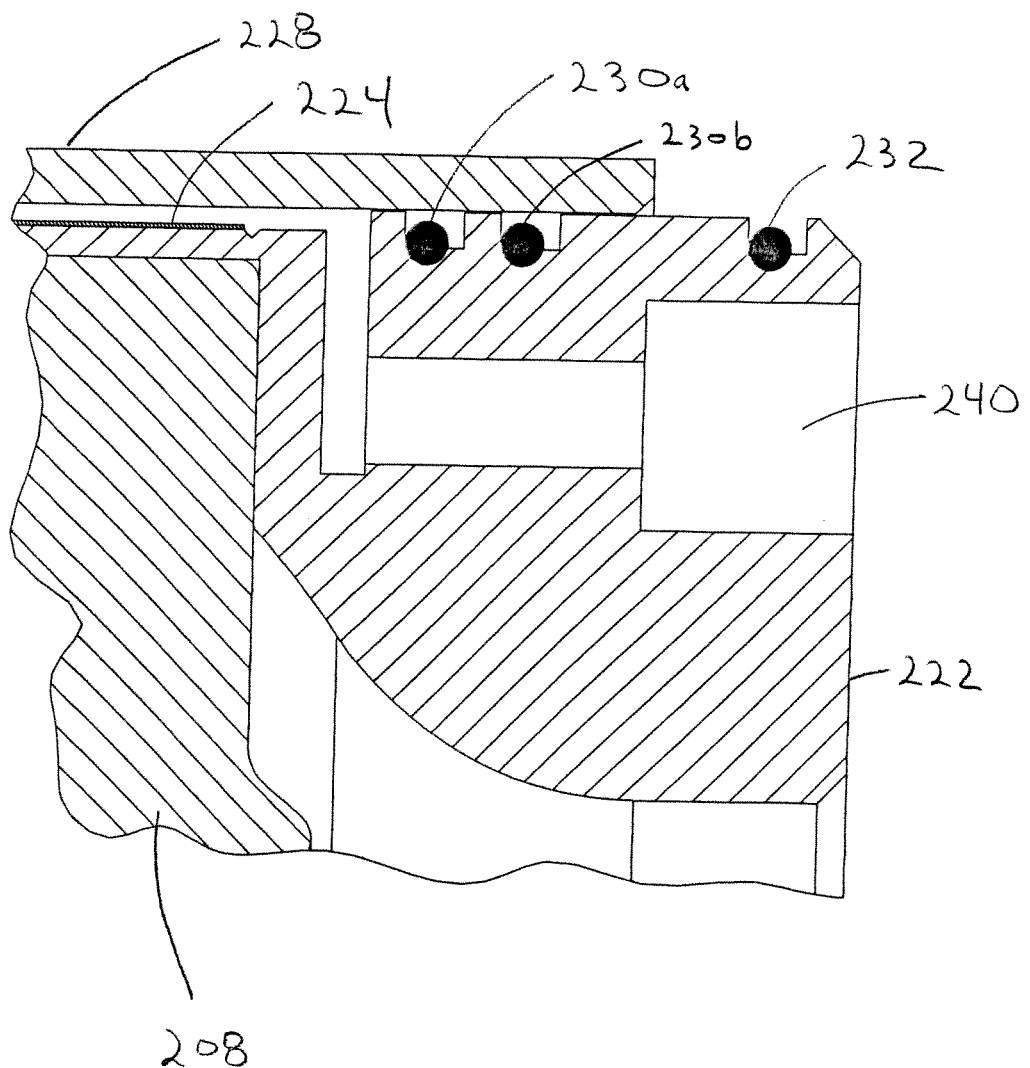
FIG. 13 is a close-up partial cross sectional view of the adsorber element embodiment shown in FIG. 10 taken along the line 13-13.
Figure 14:
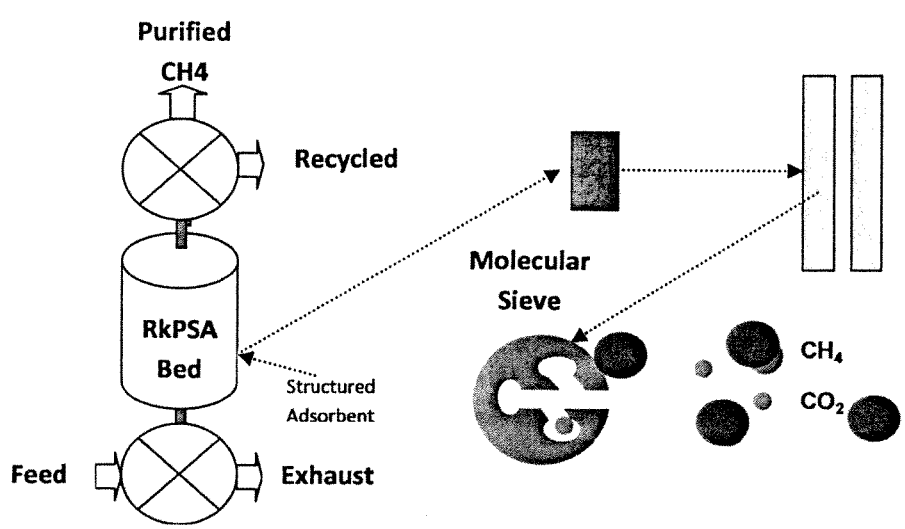
FIG. 14 is a schematic that represents the adsorption process concept.

FIGS. 10 and 11 illustrate one embodiment of an adsorber element suitable for use with embodiments of the disclosed rotary pressure swing device. As shown in FIG. 11 the adsorber element 122 includes plural adsorbent beds. For example, one embodiment includes a first radial adsorber 202, a second radial adsorber 204, a third radial adsorber 206, and a fourth radial adsorber 208. The first, second, third, and fourth radial adsorbers 202, 204, 206, 208 are laminate sheets concentrically wound about first, second, third, and fourth mandrels 210, 212, 214, 216, respectively. Spacers can be used to space adsorbers. For example, three epoxy spacer crosses 218 are positioned between the first and second radial adsorbers 202, 204, the second and third radial adsorbers 204, 206, and the third and fourth radial adsorbers 206, 208, respectively. The epoxy spacer crosses 218 help prevent axial displacement of the laminate sheets as a result of pressure fluctuations. Adsorber element 122 includes a feed bed connector 220 adjacent the first radial adsorber 202, and a product bed connector 222 adjacent to the fourth radial adsorber 208.

A button head screw 224 attaches the feed bed connector 220 to the first mandrel 210. A second button head screw 224 attaches the product bed connector 222 to the fourth mandrel 216. Set screws 226 attach the first, second, third, and fourth mandrels 210, 212, 214, 216 to each other. Housing 228 extends around the internal components of the adsorber element 122 between the feed bed connector 220 and the product bed connector 222. Two housing o-rings 230a and 230b are positioned around the feed bed connector 220, and also around the product bed connector 222, to facilitate fluidly sealing housing 228 to the feed bed connector 220 and the product bed connector 222. O-ring 230a is a sacrificial o-ring, used to stop sealant and protect o-ring 230b so it might effectively seal gas. Two connector o-rings 232 are positioned around the feed bed connector 220 and the product bed connector 222, respectively, to facilitate fluidly sealing the feed bed connector and the product bed connector to other portions of the overall rotary pressure swing device 100. For example, in the rotary pressure swing device 100, the feed bed connector 220 and the product bed connector 222 can be sealed into a product connector cavity 142 (FIG. 7) and a feed connector cavity 143 (FIG. 7), respectively.

As shown in FIG. 11, embodiments of adsorber elements (e.g., the illustrated adsorber element 112) suitable for use with embodiments of the disclosed rotary pressure swing device 100 typically include two or more sections, and each may contain a different adsorbent material or a different combination of adsorbent materials. As used herein, the term "adsorbent material" refers to particular types of adsorbent material and to particular combinations of types of adsorbent material.

In some embodiments, support structures are included to reduce displacement. Examples of support structures include the epoxy spacer crosses 218 illustrated best in FIGS. 11 and 12. Such support structures can be positioned between multiple, separate laminate structures or at one or both ends of individual laminate structures. Support structures typically include one or more elongated portions 218a (e.g., spokes) extending across the face of the laminate structures substantially perpendicular to the direction of possible displacement, such as the axial direction of spirally-wound laminate structures or the direction of fluid flow through the adsorber element. These elongated portions can be rigid or flexible and can be sized so as to minimize the disruption of fluid flow through the overall adsorber element.

The support structures can be bonded to none, one, or both of the adjacent laminate structures. In some embodiments, such as the adsorber element 122 illustrated in FIGS. 10-12, the support structures comprise an adhesive material, such as an epoxy, capable of bonding to one or both of the adjacent laminate structures. The adhesive material can be activated, for example, by heating the overall adsorber element, such as while activating the adsorbent materials. The support structures also may be solely an adhesive material, such as an epoxy. Adhesive materials often can be applied expediently to the faces of laminate structures, such as by deposition in gel form. These materials then can be allowed to set to become strong enough to resist laminate displacement.

A preferred embodiment comprises spacer cross support structures 218 that are formed by applying liquid epoxy resin to the ends of the laminate structures in the shape of a cross. A template may be employed to assist in applying beads of epoxy in order to form an appropriate cross shape 218a. The epoxy resin can thus work its way to some significant extent into the ends of the wound laminate structure and, after curing, thereby provide useful support against collapse of the windings at the ends. This can be a significant improvement over simply using preformed supports as these do not provide support between the actual winds in the laminate structure itself.

Mandrels, such as mandrels 210, 212, 214, 216 of the adsorber element 122, can be attached to inner surfaces of laminate structures and constrained from axial movement. This helps to hold the laminate structures in place. The attachment can result by any suitable means, such as by adhesive bonding. In addition, the adsorber element housing 228 can be used to help hold the laminate structures in a desired position. For example, a laminate structure can be placed into a housing 228, and then a substantially uniform concentric compressive force applied to the housing to deform it about the laminate structure to reduce or substantially prevent axial movement of the windings. To further reduce or substantially prevent movement of the laminate structures and to reduce or substantially prevent gas flow out of the housing, a bead of material, such as a ceramic material, can be placed about the inner circumference of the shell. In the adsorber element 122, a filter can be positioned to contact this bead. Other methods of fastening also can be used, such as a shoulder built into the shell. Sealants suitable for attaching laminate structures to shells include epoxy resins, such as LOCTITE® HYSOL® E-120 HP epoxy available from Henkel Corporation (Rocky Hill, Conn.). For high temperature applications (e.g., greater than about 130° C.), suitable sealants include PYRO-PUTTY® 653 available from Aremco Products, Inc. (Valley Cottage, N.Y.).

Between the laminate structures 202, 204, 206, 208 and the adsorber element housing 228 (FIG. 13) an impermeable barrier 224 can be used to prevent sealant from permeating the laminate structure 208. This impermeable barrier can be a polymer tape, or polymer sleeve, such as the shrink-wrap used to protect electrical cables. Sealant can be injected via the seal injection port 240.

Mandrels, housings and other components (e.g., support structures) of disclosed adsorber elements can be made from a variety of materials, such as metals and metal alloys (e.g. stainless steel), ceramics and/or polymeric materials. In some embodiments, the shell and/or the mandrel have a thermal conductivity at room temperature of from about 10 to about 1000 W/(m·°C.), such as from about 20 to about 1000 W/(m·°C.) or from about 50 to about 1000 W/(m·°C.). The adsorbent materials used to form laminate structures can be activated, if necessary, subsequent to insertion into the housing. In such cases, both the housing and the mandrel are sufficiently robust to withstand the adsorbent-activation temperature, such as temperatures of about 250° C. and greater. For adsorbent materials that can be activated at lower temperatures, the material used to form the shell and mandrel can be other than metals, metal alloys, ceramics, etc.

Exemplary Adsorbent and Process Specifications

Molecular sieves are materials with precise pores in the Angstrom size range.

Among different molecular sieves, Zeolitic Molecular Sieves and Carbon Molecular Sieves are used widely in gas separation processes. The most common examples used in the gas separation industry are nitrogen separation from air or carbon dioxide separation from natural gas.

Our new separation process utilizes a newly designed rapid cycle kinetic pressure swing adsorption (RkPSA) process cycle, which is tailored to match the properties of suitable adsorbent crystals, our adsorbent sheets, and our structured adsorbent. Our new process has been demonstrated to enable us to achieve methane product purities of 97%-99%, at high recoveries of 95%-99%, with minimum energy consumption of 0.2-0.3 kW per normal cubic meter per hour of feed gas.

Adsorbent:

New molecular sieves were developed to create an improved gas separation process. A novel process to purify methane from bio gas sources has been developed. The new process may utilize a selected adsorbent powder from the silica alumina phosphate family called SAPO 34. SAPO 34 is from the family of Chabazites having a chemical formula of |Ca2+6 (H2O)40|[Al12Si24O72]-CHA.

SAPO 34 molecular sieve has an 8 ring member pore with reported pore sizes in the range from 3.7-4.2° A. The Database of Zeolite Structures mentions an average pore size of 3.8 Degree Angstrom (° A). In this invention a SAPO 34 adsorbent having less than 3.9° A pore size is used to separate $CO_2$ molecules (with kinetic diameter of 3.4° A) from $CH_4$ molecules (with kinetic diameter 3.9° A). For this inventive process the specific adsorbent crystals have three important characteristics:

A. A molecular sieve pore size of less than 3.9° A, e.g. 3.8° A. Accurate pore size control is important in maintaining high kinetic selectivity by providing for fast diffusivity for $CO_2$ and slow diffusivity for $CH_4$. In this application to separate $CO_2$ (3.4° A) from $CH_4$ (3.9° A), the specific adsorbent crystals have to maintain pore sizes between these values.

B. A unimodal log-normal crystal size distribution of 10 to 80 micron is important, e.g. adsorbent having an average crystal size of 40 micron. Maintaining a unimodal and tight crystal size distribution is important in maintaining sharp kinetic selectivity. The mass transfer rate of a gas is a function of the diffusion path; hence the process is slower for large crystals than small crystals.

C. An equilibrium capacity of at least 50 cc of $CO_2$ per gram of adsorbent under standard conditions is typically desired to reach industrial performance targets for this separation application. It is expected that $CO_2$ equilibrium capacities of 70 cc/g can be achieved. Preferably up to 100 cc/g of $CO_2$ capacity can be achieved. The equilibrium capacity of SAPO 34 adsorbent for $CH_4$ is reported to be 10 cc/g. The $CH_4$ equilibrium capacity should be as low as possible, preferably as low as 5 cc/g, to maximize the equilibrium selectivity of $CO_2/CH_4$. The $CO_2/CH_4$ equilibrium selectivity of the specific adsorbent crystals under standard conditions can be as high as 20 cc/g.

Slurry:

We have discovered that the specific adsorbent crystals are unexpectedly very sensitive to the rate at which the moisture content is varied. For instance, we have noticed that the adsorbent loses a significant portion of its adsorption capacity when it suddenly comes into contact with liquid water (i.e. a sudden increase in water content) during a typical slurry preparation process (such slurries being typically used in coating process to make adsorbent sheets for adsorbent beds). This is believed to happen because the hydrogen bonds in the specific adsorbent crystals are hypersensitive and not very strong and can break off or be exchanged in the slurry solution. To minimize this capacity loss, we have developed a slow rehydration process in which we expose previously dry adsorbent to air humidity for 4-7 days. In this process moisture enters the pores in a more controlled fashion with minimum disturbance of the specific adsorbent crystals structure. After this slow rehydration, about 5-10 wt % water was found to be adsorbed in the crystals and the adsorbent does not lose capacity when subsequently put in contact with liquid water.

Drying after Coating:

A typical slurry for coating the adsorbent contains 50 wt % water. At the end of the drying process, the coated adsorbent contains 5-10 wt % water only. A conventional drying process takes only a few minutes for other adsorbents. In like manner to the above sudden increase in moisture content, the specific adsorbent crystals are also very sensitive to sudden decreases in moisture content. We have found that the adsorbent loses up to 90% of its capacity if the coated slurry is dried within in several minutes. Thus a three stage drying process has been developed to preserve the capacity of the specific adsorbent crystals during the preparation of coated adsorbent sheets. A gentle IR drying, followed by slow drying in ambient, and completed by high temperature IR treatment is explained below:

a. The adsorbent sheet is dried so as to lose 25-30% of its water by gentle IR heating (500 watts/sqft laminate) while maintaining ~40° C. coating line temperature.

b. Then the partially dried adsorbent sheet is stored for 5-10 days while it slowly loses another 5-10% of its water to the ambient atmosphere. Once the bulk of the water has evaporated from the adsorbent sheets, the sheets have to get dried further to improve the strength.

c. IR Treatment: The adsorbent sheets prepared using the specific adsorbent crystals could have strength and uniformity issues if not treated by a last faster drying stage (e.g. by IR). The otherwise low strength obtained is a direct result of less uniformity in the coating caused by migration of binder and fine particles to the surface of adsorbent sheets during drying stages. This was confirmed by observing a hard thin film of coating on the adsorbent sheet surface. Such a non-uniform porous media could become an obstacle for achieving a desired kinetic separation driving force by interfering with gas diffusion rates. In order to improve the strength of the adsorbent sheets, a rapid drying process was employed so the remaining water in the adsorbent sheets was removed without allowing binder migration. In this process the adsorbent sheets were passed through a high power IR heater zone (5000 watts/sqft laminate) reaching as high as 250° C. The high power IR treatment removes an additional 5-10% of the water without changing the particle size distribution of the coating. At the end of this stage the adsorbent sheets contain 5-10% moisture. The result of this stage is an adsorbent sheet with acceptable strength and proper moisture content.

Adsorbent Sheet:

The structured adsorbent sheets were formed with thicknesses ranging from 0.009" to 0.015". The adsorbent sheets formulation was optimized to produce low macroporosity in a range of 4% to 18% with macropore size of 0.001 to 2 micron. It is important to try and maintain such a low macroporosity in adsorbent sheets. Any macroporous media between the crystals can act as void space trapping $CH_4$ molecules and hence wasting them to the exhaust stream during a counter current blow down step. A homogenous adsorbent sheet with low macroporosity can readily be achieved by using the proper crystal size distribution mentioned previously and by using the aforementioned drying procedure.

Figure 16:
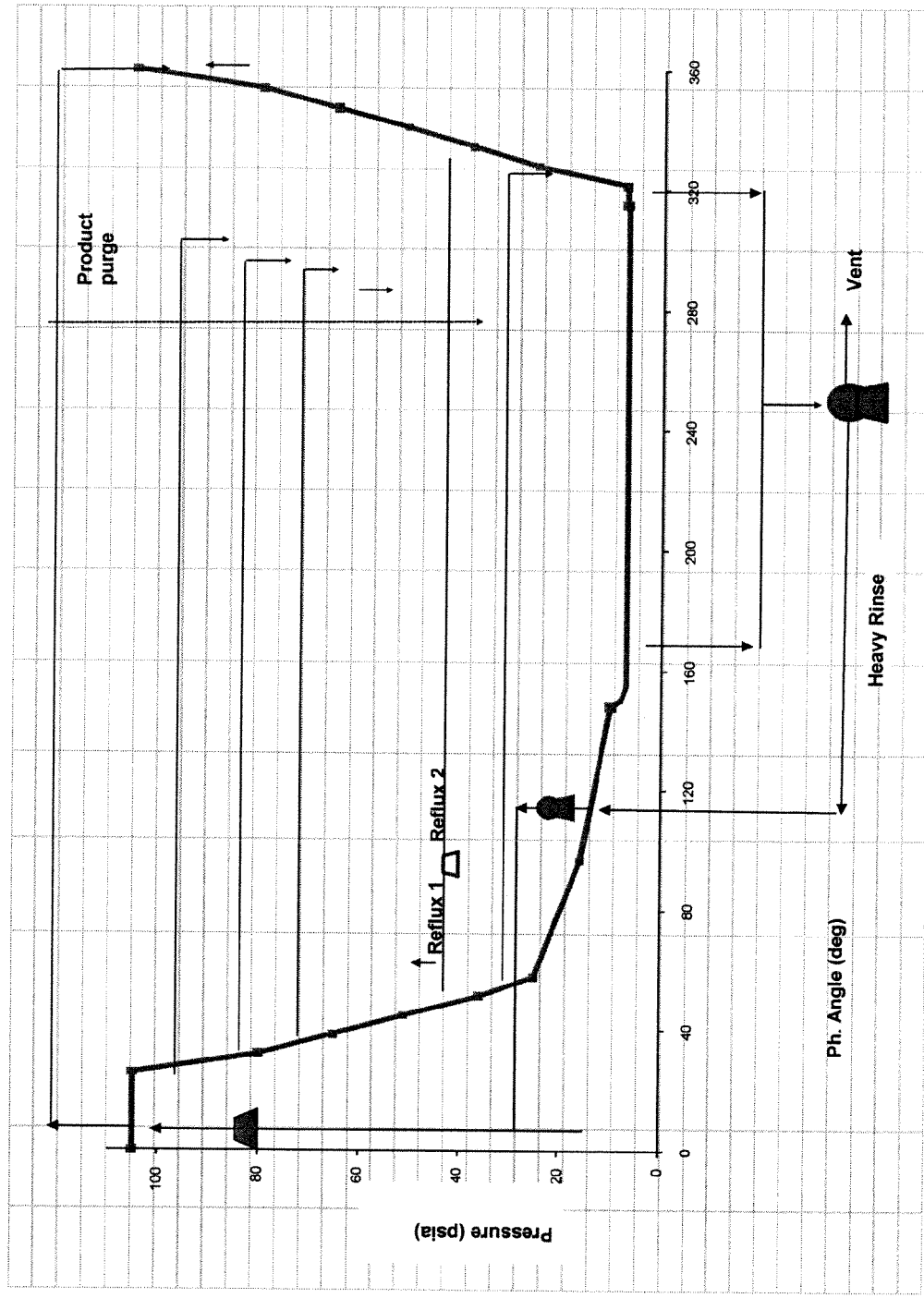
FIG. 16 is a chart of the process steps, showing the rapid kinetic pressure swing adsorption process steps and flows, with 28 beds, 5 equalization, two refluxes, and one heavy rinse.

RkPSA Cycle:

The new rapid cycle kinetic pressure swing adsorption separation works based on the differences between the kinetic size of molecules and the effective size of the adsorbent pores, hence is called kinetic pressure swing adsorption or kPSA. This process is described below in text, and in FIGS. 15-16.

A brief description of the RkPSA process is that when the bed pressure increases, $CO_2$ molecules, which are smaller compared to the adsorbent pore size, diffuse rapidly through the adsorbent pores and into the adsorption sites. However, the $CH_4$ molecules, which are larger compared to the adsorbent pore size, cannot diffuse into the adsorbent pores in a short production step. Hence $CH_4$ molecules occupy mainly the gas phase in the bed void space. The bed void space generally consists of the gas channels and macroporous media of adsorbent sheets. The result is an increased concentration of methane in the gas phase which exits the bed from the product port as purified methane during the production step. Hence once the bed pressure increases to its maximum level, the product valve opens to withdraw the purified methane from the bed.

The product step continues until the adsorbent pores are mainly occupied by $CO_2$ molecules. At this point the product valve shuts off to prevent low purity methane breakthrough. The product step should be shorter than the time that $CH_4$ needs to diffuse into the crystals. This helps maintaining high $CH_4$ concentration in equalization steps and high $CO_2$ concentration in exhaust steps.

At the end of the production step there is still a significant amount of $CH_4$ in the bed at high pressure to be recovered. Recovery of the left over gas from the adsorbent vessels is done by using several recycle streams inside and outside of the RkPSA machine.

Internal recycle streams are utilized for equalization steps. The time that the adsorbent beds spend in equalization steps should be shorter than the time required for $CO_2$ to diffuse out of the adsorbent crystals. In other words, the rate of equalization is faster than the rate of diffusion of $CO_2$ out of the adsorbent. This helps maintain high $CH_4$ concentration in the equalization steps and high $CO_2$ concentration in the exhaust steps.

In a preferred embodiment, the external recycle streams are utilized for two external refluxes. The first reflux stream recovers $CH_4$ gas from bed voids until the bed pressure drops close to atmospheric pressure. The second reflux stream recovers the additional $CH_4$ from the bed void spaces under vacuum. To recover the remaining $CH_4$ trapped in the bed void space a heavy rinse stream pushes high $CO_2$ content of exhaust gas to the bottom of the bed. The $CO_2$ moves up in the bed while diffusing into all bed void spaces and adsorbent sheet macropores. This action pushes the $CH_4$ gas out of the voids and macropores and towards the product end of the bed.

Once most of the $CH_4$ is recovered from a bed, the exhaust valve opens to depressurize the bed, thereby helping $CO_2$ molecules exit the adsorbent pores and eventually the adsorbent beds. The exhaust step has to be long enough to remove all $CO_2$ from the adsorbent sites. It should also be long enough to help $CH_4$ diffuse out of the adsorbent.

This process is repeated on all beds sequentially to generate steady state product and exhaust flows. The frequency of the cycle is 30 CPM, but it could be anywhere from 1 to 100 CPM.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim

1. A gas separation device for separating carbon dioxide from a gas mixture comprising methane and carbon dioxide, comprising a rapid cycle kinetic pressure swing adsorption apparatus comprising an adsorbent structure, the adsorbent structure comprising a kinetic adsorbent comprising a molecular sieve with an average pore size of less than about 3.9 Angstroms, wherein the molecular sieve is a silica alumina phosphate.

2. The gas separation device of claim 1 wherein the molecular sieve has an average pore size greater than about 3.7 Angstroms.

3. The gas separation device of claim 1 wherein the silica alumina phosphate is SAPO 34.

4. The gas separation device of claim 3 wherein the crystal size distribution of the SAPO 34 is between about 10 and about 80 microns.

5. The gas separation device of claim 4 wherein the average crystal size of the SAPO 34 is about 40 microns.

6. The gas separation device of claim 1 wherein the adsorbent structure is characterized by a macroporosity between 4% and 18%.

7. The gas separation device of claim 1 wherein the adsorbent structure is characterized by a macropore size between about 0.001 microns and about 2 microns.

8. The gas separation device of claim 1 wherein the adsorbent structure is a parallel passage structured adsorbent comprising a laminated adsorbent sheet.

9. The gas separation device of claim 1 wherein the rapid cycle kinetic pressure swing adsorption apparatus is a rotary rapid cycle kinetic pressure swing adsorption apparatus.

10. A gas separation device for separating carbon dioxide from a gas mixture comprising methane and carbon dioxide, comprising a rotary rapid cycle kinetic pressure swing adsorption apparatus comprising an adsorbent structure, the adsorbent structure comprising a kinetic adsorbent comprising a molecular sieve with an average pore size of less than about 3.9 Angstroms and greater than about 3.7 Angstroms, wherein the molecular sieve is a silica alumina phosphate.

11. A gas separation device for separating carbon dioxide from a gas mixture comprising methane and carbon dioxide, comprising a rotary rapid cycle kinetic pressure swing adsorption apparatus comprising an adsorbent structure, the adsorbent structure comprising a kinetic adsorbent comprising a molecular sieve with an average pore size of less than about 3.9 Angstroms and greater than about 3.7 Angstroms, and wherein the molecular sieve is SAPO 34.

* * * * *